United States Patent [19]
Sobel

[11] Patent Number: 5,334,155
[45] Date of Patent: Aug. 2, 1994

[54] HYPODERMIC SYRINGE NEEDLE GUARD

[76] Inventor: Daniel Sobel, 2113 Carriage Sq., Silver Spring, Md. 20906

[21] Appl. No.: 43,293

[22] Filed: Apr. 6, 1993

[51] Int. Cl.$^5$ .............................................. A61M 5/00
[52] U.S. Cl. ..................... 604/110; 604/192
[58] Field of Search ............... 604/110, 187, 192, 198, 604/263

[56] References Cited

U.S. PATENT DOCUMENTS 4,986,819  1/1991  Sobel ............................. 604/192 X

*Primary Examiner*—John D. Yasko
*Attorney, Agent, or Firm*—Hodgson, Russ, Andrews, Woods & Goodyear

[57] ABSTRACT

A needle guard for a hypodermic syringe to prevent repuncture by a used needle. The needle guard comprises a flexible double-walled membrane which is shaped to define a closed toroidal chamber which, under atmospheric pressure, is conical in shape and defines a hollow interior with an opening thereto for passage of the needle. The toroidal chamber is partially evacuated and folded inwardly upon itself with a needle passing through the opening for normal use of the needle. Upon release of the partial vacuum, the entrance of air into the toroidal chamber effects expansion of the needle guard into the shape of a cone with the needle contained within the hollow interior thereof so that needle-stick or re-use of the needle may be prevented.

20 Claims, 2 Drawing Sheets

HYPODERMIC SYRINGE NEEDLE GUARD

Reference is made to disclosure document 289,577, which discloses the present invention.

The present invention relates to a protective covering for a hypodermic needle for preventing needle-stick or re-use thereof. More particularly, the present invention relates to a protective needle guard that is expandable to cover the injecting tip of a hypodermic needle.

A needle protective sleeve is disclosed in U.S. Pat. No. 4,772,272 to McFarland.

The need to prevent repuncture with a used syringe needle has become of paramount inportance in view of the AIDS epidemic. Laboratory personnel and doctors may have become accidently infected with the AIDS virus by puncturing themselves with needles used to inject or draw blood from an AIDS-infected patient.

A pressure-sensitive needle guard is disclosed in my U.S. Pat. No. 4,986,819, which is incorporated herein by reference, for the purposes of preventing repuncture.

It is an object of the present invention to provide an improved needle guard for hypodermic syringes.

In accordance with the present invention a needle guard comprises a flexible double-walled membrane which is shaped to define a closed toroidal chamber which, prior to the use of the needle, is in an inwardly folded position. After use of the needle, the toroidal chamber may be pressurized to cause its expansion into a generally conical shape covering the needle tip.

The above and other objects, features, and advantages of the present invention will be more apparent in the following detailed description of the preferred embodiments thereof when taken in conjunction with the accompanying drawings wherein like reference numerals denote the same or similar parts throughout the several views.

DETAILED DESCRIPTION OF THE PREFERRED EMBODIMENTS

Figure 1:
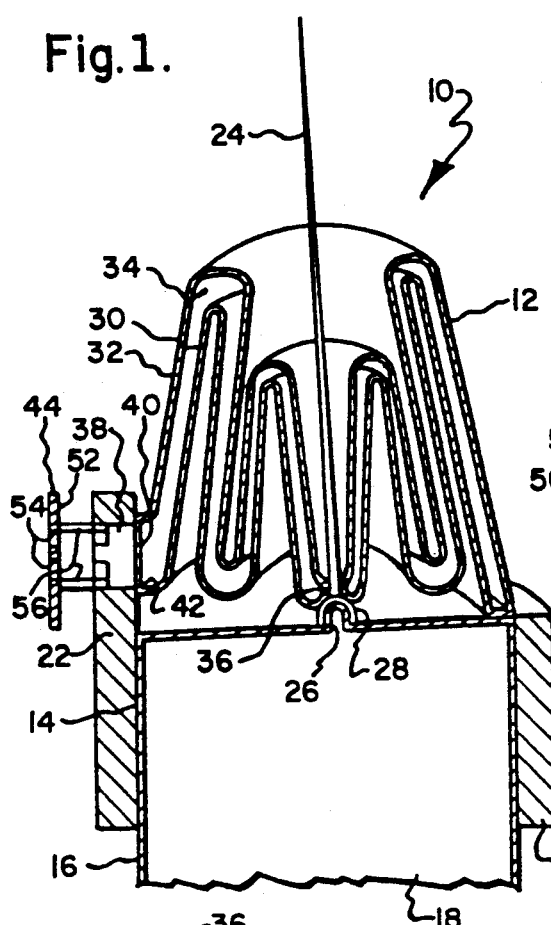
FIG. 1 is a sectional view of a needle guard which embodies the present invention and which is illustrated attached to a hypodermic syringe in a folded condition prior to use of the needle.
Figure 2:
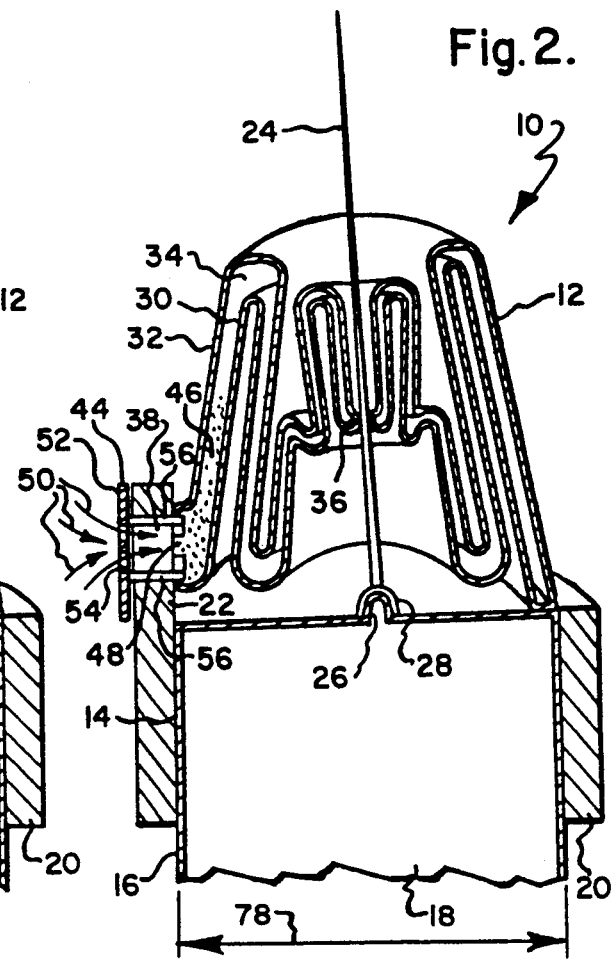
FIG. 2 is a view similar to that of FIG. 1 illustrating the needle guard in the process of being expanded under pressurization.
Figure 3:
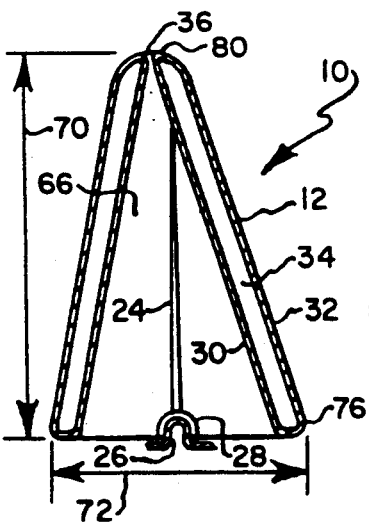
FIG. 3 is a generally schematic sectional view illustrating the needle guard after it has been fully expanded for protection of the needle against re-use.

Referring to FIG. 1, there is illustrated at 10 a needle guard which is composed of a thin flexible membrane 12 which is foldable, such as shown in FIG. 1, and which is unfoldable when pressurized, as shown in FIGS. 2 and 3.

The membrane 12 is suitably attached to the forward portion 14 of a barrel 16 of a hypodermic syringe 18 via a rigid collar 20 which has an extension portion 22 the purpose of which will be discussed in greater detail hereinafter.

A hypodermic needle 24 attaches to a nose abutment 26 of the syringe 18 by means of a slide-on cap 28.

Referring to FIG. 3, in order to alleviate the need for sealing between the needle guard 10 and the needle 24 or other parts of the syringe 18, in accordance with the present invention the needle guard 10 is a double-walled structure having inner and outer walls 30 and 32 respectively which define between them a closed toroidal chamber 34 in the shape of a hollow cone. The needle guard has a diameter, illustrated at 72, at its inner end 76 substantially equal to the barrel diameter, illustrated at 78, for attachment thereto, and the toroidal shape defines a hollow interior 66 with an opening 36 thereto at the outer end 80 which is sized for passage of the needle 24. The opening 36 is thus sized only slightly larger than the needle diameter. It should be understood that the opening 36 is not in the membrane 12, but the membrane toroidally surrounds the opening 36, which defines an entrance to the space or hollow 66 which the inner wall 30 of toroidal membrane 12 circumscribes when in the conical shape. As seen in FIG. 3, when activated for protection against needle-stick, the needle guard 10 has a length, illustrated at 70, which allows it to extend beyond the tip of the needle so that the needle is protectively enclosed within the hollow interior 66 of the guard. The membrane 12 is preferably constructed to have a shape so that, when activated, it extends asymmetrically over the needle 24, as illustrated in FIG. 3, to further protectively enclose the needle. When the membrane is conically shaped as in FIG. 3, the end portion 80 may be said to be the vertex thereof. The needle guard 10 may be injection molded or otherwise suitably manufactured using principles commonly known to those of ordinary skill in the art to which this invention pertains. Therefore, the process for manufacture thereof will not be described in detail herein.

Referring again to FIG. 1, the guard 10 may be folded into an inactive position, so that the syringe 18 may be used, by at least partially evacuating the chamber 34 to form a partial vacuum therein, using principles commonly known to those of ordinary skill in the art to which this invention pertains, while folding the double-walled membrane 12 inwardly in a series of folds while allowing the needle 24 to pass through the opening 36. While FIG. 1 shows the walls 30 and 32 spaced apart for ease of illustration, it should be understood that with the resulting partial vacuum, the walls 30 and 32 would tend to come together.

Figure 4:
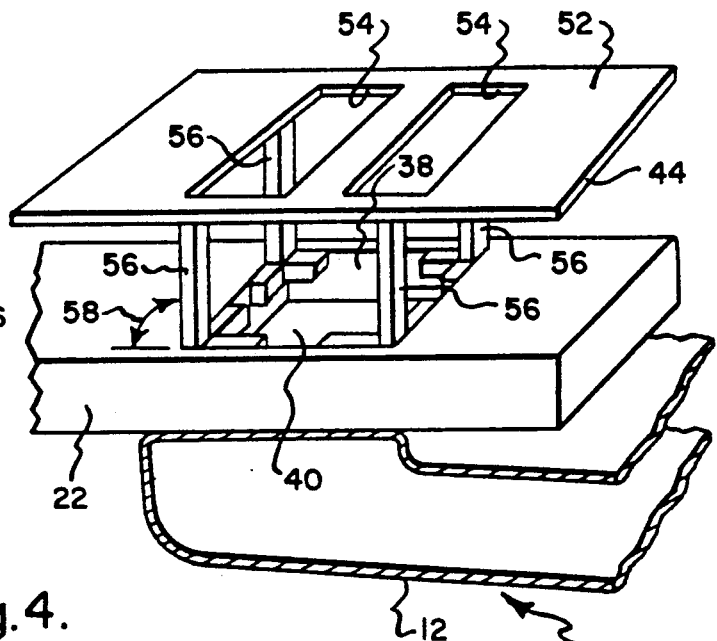
FIG. 4 is a perspective view of a push button member for rupturing the membrane of the needle guard of FIG. 1 for pressurization thereof.
Figure 5:
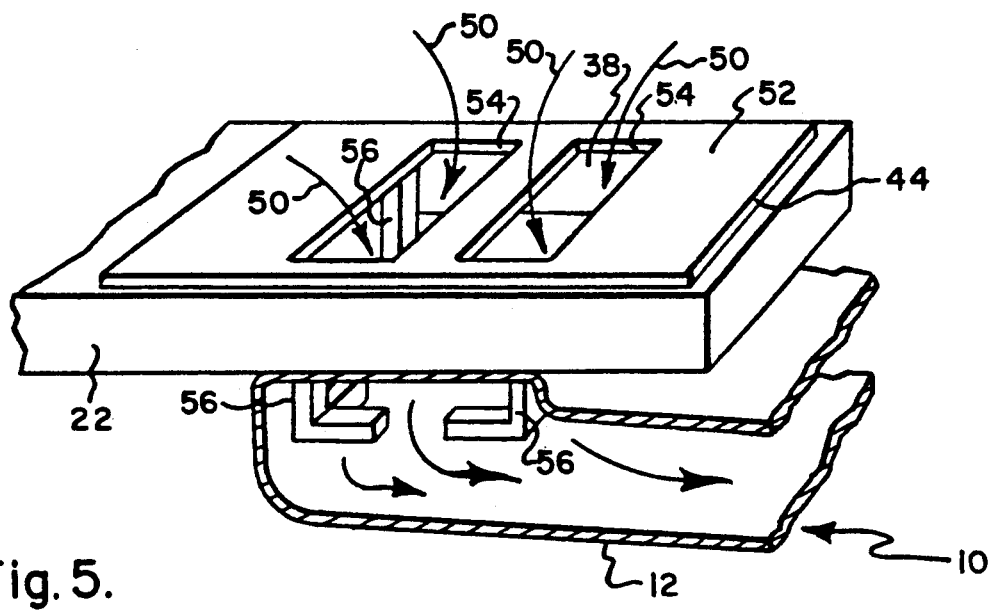
FIG. 5 is a perspective view of the push button of FIG. after rupture of the membrane.

The rigid extension portion 22 has an opening 38 therethrough, and a wall portion, illustrated at 40, of the needle guard membrane is suitably attached to the extension portion 22 across the opening 38 and is preferably scored at 42 so that it is pre-weakened. Within the opening 38 is provided a push button device 44 which may be pushed within the opening to engage the membrane 12 for puncturing a hole therein so that air, illustrated at 46 in FIG. 2, may flow through the punctured hole, illustrated at 48, in the membrane and into the toroidal chamber 34 as illustrated by arrows 50. The push button 44 includes an outer stop member 52 in which are contained air-receiving apertures, illustrated at 54 in FIGS. 4 and 5, and a plurality of perhaps four membrane engagement members 56, each for a corner of the generally rectangular opening, for puncturing the hole 48 in the membrane. However, it should be understood that the push button 44 may have any other suitable shape for achieving the objective of puncturing a hole in the membrane 12.

The push button 44 is preferably sized relative to the opening 38 so that it is press-fit therein so as not to be lost from the opening during normal shipment and handling. In order to achieve such a tight fit, the members 56 are oriented so as to form an angle, illustrated at 58, with the extension portion 22 of slightly more than 90 degrees, for example, perhaps about 90.5 degrees.

Referring to FIG. 2, as air 46 rushes into the evacuated chamber 34 upon puncturing of the hole 48 in the membrane 12, it effects a tendency of the needle guard 10 to straighten into the conical configuration of FIG. 3 with the outer end defining the opening 36 sliding up the needle 24 toward and beyond the needle tip so that the needle tip is within the hollow interior 66 defined by the inner wall 30 of the toroidal needle guard 10.

The provision of the rigid extension portion 22 for attachment of the membrane 12 is provided to allow the membrane to be more easily punctured in that the membrane portion 40 is restricted from flexing as it is engaged by the push button members 56.

Suitable membrane materials include, but are not limited to, polyethylene and polypropylene. These materials are considered tough enough to prevent the tip of the needle from penetrating therethrough yet allow the membrane 12 to suitably expand as it is pressurized to atmospheric pressure.

Alternatively, the membrane 12 may be composed of latex or other suitable thin rubber or plastic material with the portion of the membrane 12 around the hole 36 composed or overlaid with a harder, more resistant to needle puncture, material such as, for example, polyethylene or polypropylene.

Figure 6:
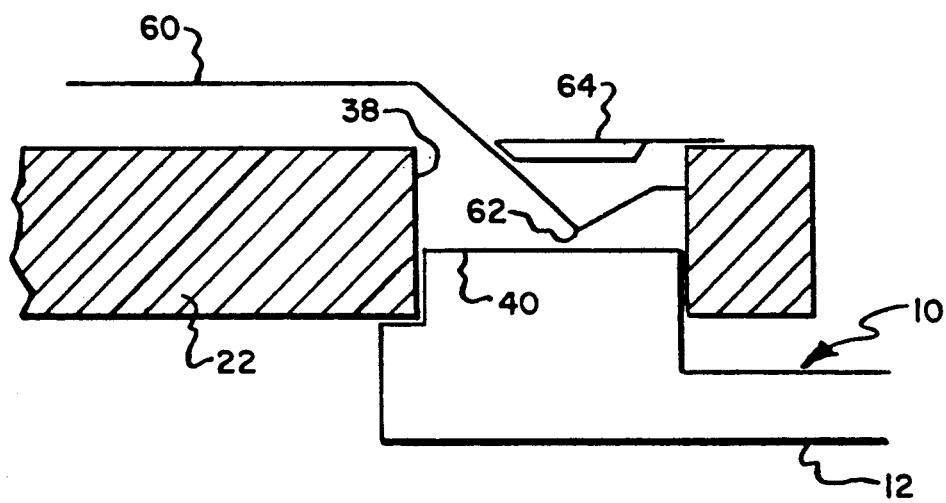
FIG. 6 is a schematic view illustrating an alternative embodiment of the push button device for rupturing the membrane, shown prior to membrane rupture.
Figure 7:
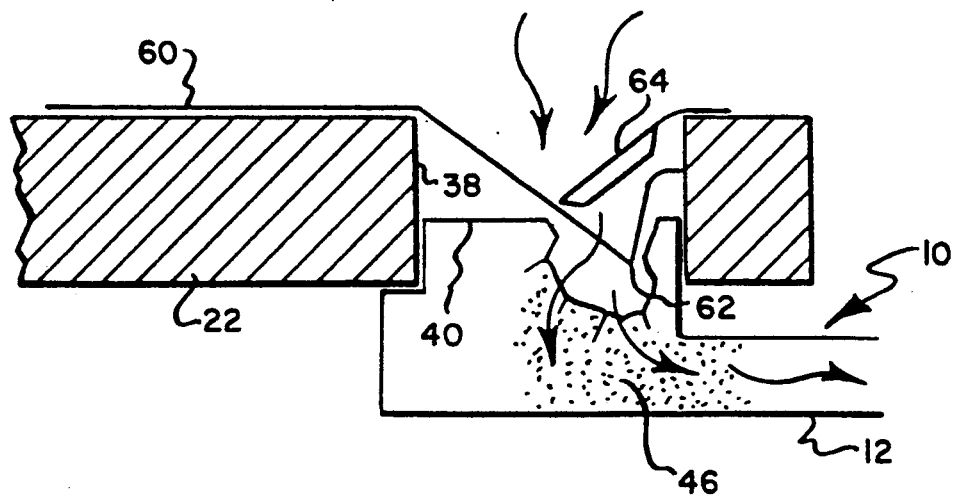
FIG. 7 is a view similar to that of FIG. 6 showing the alternative device after rupture of the membrane.

Referring to FIGS. 6 and 7, there is shown an alternative embodiment of puncturing means for the needle guard 10. Similarly as for FIGS. 4 and 5, the membrane 12 is attached to the extension portion 22 so as to have a portion 40 which extends across the hole 38. A suitable member 60 having a point 62, which may be a blade, is flexibly attached to the extension portion 22 to extend across the opening 38. Lever 64 is also flexibly attached to the extension portion 22 to extend into the opening 38 and to engage member 60, upon pushing thereof with one's finger, to cause inward movement of the point 62 into the membrane portion 40 to thereby puncture it, as shown in FIG. 7, to allow the entrance of air 46.

It should be understood that while the invention has been described in detail herein, the invention can be embodied otherwise without departing from the principles thereof. For example, the needle guard may have a compressed gas chamber as described in my aforesaid patent. Such other embodiments are indeed meant to come within the scope of the present invention as defined in the appended claims.

What is claimed is:

1. A needle guard for a hypodermic syringe comprising, a flexible membrane which is shaped to define a toroidal chamber which, under a first pressure, is conical in shape and includes one end portion having an opening means sized for passage of the needle, an other end portion sized for attachment to a forward portion of a barrel of the hypodermic syringe, and a length to extend beyond the tip of the needle, the membrane further shaped so that the toroidal chamber extends around the needle when the needle guard is attached to the hypodermic syringe whereby the needle does not extend into the toroidal chamber, said membrane chamber being closed and under a second pressure less than said first pressure and folded inwardly upon itself so that the needle passes within said opening means and beyond the membrane, means for attachment of said other end portion to the forward portion of the barrel of the hypodermic syringe, and means for applying said first pressure to said chamber to effect unfolding of the membrane to cover the needle tip for preventing needle-stick or re-use of a used hypodermic needle.

2. A needle guard according to claim 1 wherein said pressure applying means comprises a rigid member which is attachable to the forward portion of the barrel of the hypodermic syringe for extending outwardly beyond the barrel, means defining an opening in said rigid member, said membrane attached to said rigid member so that a membrane portion extends across said rigid member opening means, and means for rupturing said membrane portion.

3. A needle guard according to claim 2 wherein said rupturing means comprises a push button disposed at least partially within said rigid member opening means for movement into rupturing engagement with said membrane portion.

4. A needle guard according to claim 3 wherein said push button is press-fit in said rigid member opening means.

5. A needle guard according to claim 3 wherein said membrane portion is scored to be pre-weakened for rupturing thereof.

6. A needle guard according to claim 1 wherein said membrane has a shape to extend asymmetrically over the needle when under said first pressure.

7. A needle guard for a hypodermic syringe comprising a flexible membrane which is shaped to define a toroidal chamber which, under a first pressure, is conical in shape and includes one end portion having an opening means sized for passage of the needle, an other end portion sized for attachment to a forward portion of a barrel of the hypodermic syringe, and a length to extend beyond the tip of the needle, the membrane further shaped so that the toroidal chamber extends around the needle when the needle guard is attached to the hypodermic syringe whereby the needle does not extend into the toroidal chamber, and which, when closed and under a second pressure less than said first pressure, is foldable inwardly upon itself so that the needle passes within said opening means and beyond the membrane for use thereof, means for attachment of said other end portion to the forward portion of the barrel of the hypodermic syringe, and means for applying said first pressure to said chamber to effect unfolding of the membrane to cover the needle tip for preventing needle-stick or re-use of a used hypodermic needle.

8. A needle guard according to claim 7 wherein said membrane has a shape to extend asymmetrically over the needle when under the first pressure.

9. A needle guard according to claim 7 wherein said first pressure is atmospheric pressure and said second pressure is a partial vacuum.

10. A needle guard according to claim 7 wherein said pressure applying means comprises a rigid member which is attachable to the forward portion of the barrel of the hypodermic syringe for extending outwardly beyond the barrel, means defining an opening in said rigid member, said membrane attached to said rigid member so that a membrane portion extends across said rigid member opening means, and means for rupturing said membrane portion.

11. A needle guard according to claim 10 wherein said rupturing means comprises a push button disposed at least partially within said rigid member opening means for movement into rupturing engagement with said membrane portion.

12. A needle guard according to claim 11 wherein said push button is press-fit in said rigid member opening means.

13. A needle guard according to claim 11 wherein said membrane portion is scored to be pre-weakened for rupturing thereof.

14. A needle guard for a hypodermic syringe comprising a flexible membrane which is shaped to define a toroidal chamber which, under atmospheric pressure, is conical in shape and includes one end portion having an opening means sized for passage of the needle, an other end portion sized for attachment to a forward portion of a barrel of the hypodermic syringe, and a length to extend beyond the tip of the needle, the membrane further shaped so that the toroidal chamber extends around the needle when the needle guard is attached to the hypodermic syringe whereby the needle does not extend into the toroidal chamber, said membrane chamber being closed and at least partially evacuated and folded inwardly upon itself so that the needle passes within said opening means and beyond the membrane, means for attachment of said other end portion to the forward portion of the barrel of the hypodermic syringe, and means for applying a first pressure to said chamber to effect unfolding of the membrane to cover the needle tip for preventing needle-stick or re-use of a used hypodermic needle.

15. A needle guard according to claim 14 wherein said membrane has a shape to extend asymmetrically over the needle when under atmospheric pressure.

16. A needle guard according to claim 14 wherein said pressure applying means comprises a rigid member which is attachable to the forward portion of the barrel of the hypodermic syringe for extending outwardly beyond the barrel, means defining an opening in said rigid member, said membrane attached to said rigid member so that a membrane portion extends across said rigid member opening means, and means for rupturing said membrane portion.

17. A needle guard according to claim 16 wherein said rupturing means comprises a push button disposed at least partially within said rigid member opening means for movement into rupturing engagement with said membrane portion.

18. A needle guard according to claim 17 wherein said push button is press-fit in said rigid member opening means.

19. A needle guard according to claim 17 wherein said membrane portion is scored to be pre-weakened for rupturing thereof.

20. In combination with a hypodermic syringe including a barrel having a forward portion and a needle attached to said forward portion, a needle guard comprising a flexible membrane which is shaped to define a toroidal chamber which includes one end portion having an opening means sized for passage of the needle and includes an other end portion attached to said forward portion of said barrel of the hypodermic syringe and which, under a first pressure, is conical in shape and extends beyond the tip of the needle, the toroidal chamber extending around the needle whereby the needle does not extend into the toroidal chamber, and which, when closed and under a second pressure less than said first pressure, is foldable inwardly upon itself so that the needle passes within said opening means and beyond the membrane for use thereof, and means for applying said first pressure to said chamber to effect unfolding of the membrane to cover the needle tip for preventing needle-stick or re-use of a used hypodermic needle.

* * * * *